(12) United States Patent
Cumbie

(10) Patent No.: US 6,960,201 B2
(45) Date of Patent: Nov. 1, 2005

(54) METHOD FOR THE PREVENTION AND TREATMENT OF SKIN AND NAIL INFECTIONS

(75) Inventor: William Emmett Cumbie, Yorktown, VA (US)

(73) Assignee: Quanticum, LLC, Yorktown, VA (US)

( * ) Notice: Subject to any disclaimer, the term of this patent is extended or adjusted under 35 U.S.C. 154(b) by 275 days.

(21) Appl. No.: 10/215,834

(22) Filed: Aug. 9, 2002

(65) Prior Publication Data

US 2003/0153962 A1 Aug. 14, 2003

Related U.S. Application Data

(60) Provisional application No. 60/355,088, filed on Feb. 11, 2002.

(51) Int. Cl.[7] .............................................. A61B 18/18
(52) U.S. Cl. .............................. 606/9; 606/3; 607/88; 607/89; 607/91; 128/898
(58) Field of Search .................... 606/3, 9; 607/88–91; 128/898

(56) References Cited

U.S. PATENT DOCUMENTS

| | | | |
|---|---|---|---|
| 4,930,504 A | * | 6/1990 | Diamantopoulos et al. ... 607/88 |
| 5,900,211 A | | 5/1999 | Dunn et al. |
| 5,947,956 A | * | 9/1999 | Karell ........................... 606/9 |
| 5,968,986 A | | 10/1999 | Dyer |
| 6,022,549 A | | 2/2000 | Dyer |
| 6,090,788 A | * | 7/2000 | Lurie .......................... 514/23 |
| 6,129,893 A | | 10/2000 | Bolton et al. |
| 6,183,773 B1 | | 2/2001 | Anderson |
| 6,254,625 B1 | | 7/2001 | Rosenthal |
| 6,283,986 B1 | | 9/2001 | Johnson |
| 6,663,659 B2 | * | 12/2003 | McDaniel .................... 607/88 |
| 6,706,032 B2 | * | 3/2004 | Weaver et al. .............. 604/500 |
| 2002/0161418 A1 | | 10/2002 | Wilkens |
| 2003/0023284 A1 | * | 1/2003 | Gartstein et al. ............. 607/88 |

OTHER PUBLICATIONS

FOA, *Kinetics of Microbial Inactivation for Alt. Food Processing Tech.–Pulsed Light Tech.*, Jun. 2, 2000, 9 pgs, Wash. D.C.
EPA, *The EPA Guidance Manual on Alt. Disinfectants*, Chapter 8, Apr.–1999, 24 pgs., Wash. D.C.
The Health Physics Society, *Ultraviolet Radiation and the Public Health*, Jul. 1998, 2 pgs, McLean, VA.
American Ultraviolet Company, *Determining UV Intensity and UV Inactivation Charts*, No Date, 5 pgs., Murray Hill, NJ.
Atlantic Ultraviolet Company, *UV Inactivation Charts*, 2001, 2 pgs. Hauppauge, NY.
World Health Org., *Health and Environmental Effectcs of UV Rad.*, 1995, 8 pages, New York, NY, Ref. Fig. 3.
Conner–Kerr, *Effects of UVC on a Perineal Inf. by C. Albicans in a Female Wi Type 2 Diabetes.*, After Dec. 2001, Abstract for Poster Session at the 15th Annual Symposium on Advanced Wound Care (Apr., 2002).

* cited by examiner

*Primary Examiner*—A. Farah
(74) *Attorney, Agent, or Firm*—Merek, Blackmon & Voorhees

(57) ABSTRACT

A method of prevention and treatment of microbial infections that occur on, or just below, the skin and nails consisting of the application of electromagnetic radiation to an infected area of skin or nails for a time and at a proximity and intensity sufficient to render the microbes substantially inactivated and incapable of reproducing.

23 Claims, 1 Drawing Sheet

METHOD FOR THE PREVENTION AND TREATMENT OF SKIN AND NAIL INFECTIONS

CROSS-REFERENCE TO RELATED APPLICATIONS

This application claims the benefit of PPA Ser. No. 60/355,088 with filing date of Feb. 11, 2002.

FEDERALLY SPONSORED RESEARCH

NOT APPLICABLE

SEQUENCE LISTING OR PROGRAM

NOT APPLICABLE

BACKGROUND

1. Field of Invention

This invention relates to preventing and treating skin and nail infections using electromagnetic radiation.

2. Background of the Invention

The germicidal effects of electromagnetic radiation have been recognized for many years. Currently, electromagnetic radiation is being used more frequently at water and wastewater treatment plants to render water-borne pathogens harmless. Additionally, electromagnetic radiation is used to sterilize and purify air, particularly in laboratories and medical establishments. It is also used to sterilize equipment at such establishments. Electromagnetic radiation has been used for several years to sterilize and disinfect food products and has also been used to sanitize the hands to prevent the spread of germs to other persons.

However, the germicidal effects of electromagnetic radiation have not been recognized as a method for the prevention and treatment of skin and nail infections. Electromagnetic radiation is frequently combined with other additional chemical compositions to treat existing psoriasis, rashes, and other non-infectious skin disorders. It is believed that this type of treatment, termed phototherapy, is effective because it has an immunosuppressive effect that permits the body to heal itself. Recently, lasers alone have been successfully used to treat psoriasis by clearing localized chronic plaque. Phototherapy is also used to treat jaundice which is also a non-infectious disorder. However, no method of using electromagnetic radiation alone has been discovered to successfully treat existing microbial infections nor has electromagnetic radiation been used as a preventative treatment for infections.

Perceived Inability of Germicidal Radiation to Penetrate Skin and Nails

The main reason that electromagnetic radiation (also referred to as 'radiation' in this application) alone has not been used to prevent and treat skin and nail infections is that radiation generally considered germicidal is in the UVC range and has a perceived inability to penetrate the skin and nails deeply enough to inactivate the organisms that cause infection. It is well known that electromagnetic radiation cannot readily penetrate solid objects, particularly if the wavelength of such radiation is short. Very short wavelength light can even be absorbed by a relatively transparent media such as air. Ultraviolet light is a prime example of this with all of the ultraviolet C light (wavelength 100 to 280 nm) generated by the Sun being absorbed by the atmosphere before it reaches earth. Debris and other items also can prevent radiation from penetrating items. However, electromagnetic radiation can penetrate deep enough to inactivate organisms if it is applied for sufficient time and intensity. The Health Physics Society in its July 1998 paper titled "Ultraviolet Radiation and the Public Health" notes that "UVC, used in germicidal lamps, causes almost no damage because of its low penetration of the skin." INTERSUN, the global UV project sponsored by the United Nations contains a graphic showing only 5% of UVC (at 254 nm) can penetrate to approximately a quarter of the depth of the epidermis and less than 1% can penetrate more than half the depth of the epidermis. Many other sources indicate that UVC cannot penetrate the skin or can do so only to a very limited depth. However, this depth is sufficient to treat infections since organisms are particularly susceptible to germicidal radiation. Also, with respect to nail infections, the additional radiation required to penetrate the nail is not harmful to the nail since it is composed of dead keratin.

UVC Dose Necessary to Inactivate Microbes

A second major reason the use of UV has not been contemplated are the relatively high doses necessary to kill some types of organisms. However, it has been found that it is not always necessary to kill organisms to render them harmless. It has been shown that organisms can be inactivated and rendered harmless using far less radiation than is necessary to kill them. Therefore, although its use as a treatment for has been overlooked in the past, electromagnetic radiation of sufficient strength can be used to treat human and animal infections.

There are several publications that note that organisms can be rendered harmless with less energy than is necessary to kill them. The inactivation of organisms by damaging RNA and DNA and preventing them from reproducing is a method used for disinfection of highly transparent potable water and is discussed in more detail in U.S. Pat. No. 6,129,893 (Bolton, 2000). The patent describes a method for preventing the replication of *Cryptosporidium parvum* using ultraviolet light. This patent indicates that ultraviolet light can inactivate bacteria at doses that are 3% to 10% of the dose necessary to actually kill the organisms. The method of inactivation is described as damage to the DNA and RNA that prevents the organisms from replicating. Since organisms are not long-lived in themselves, they are unable to continue to cause infection if they are unable to replicate. This discovery is applied to the inactivation of a pathogen in drinking water to render it safe for consumption. However, the method is only to irradiate one type of organism and then only in highly transparent drinking water.

The EPA guidance manual on Alternate Disinfectants and Oxidants (April 1999) devotes Chapter 8 to a discussion of germicidal UV as a disinfectant for drinking water. The manual notes that a UV wavelength of 240 to 280 nm is highly absorbed by the RNA and DNA of a microorganism. The absorbance of UV by the organisms results in the damage to the organism's ability to reproduce. The damage is often caused by the dimerization of pyrimidine molecules. This distorts the DNA helical structure. The EPA guidance manual also notes that the dose to inactivate 90% of most types of organisms is very low with a typical range of 2 to 6 $mJ/cm^2$. The manuals notes that the germicidal radiation can be generated by a number of sources including a low pressure mercury lamp emitting at 254 nm, a medium pressure lamp emitting at 180 to 1370 nm, or lamps that emit at other wavelengths in a high intensity pulsed manner.

It should also be noted that it is not necessary to kill and inactivate all organisms in order to effect a cure for an infection. If a substantial amount of the organisms that have caused an infection are destroyed or rendered inactivated, the body's natural defenses will often work to clear the infection. Thus, doses of radiation necessary to effect a cure for an infection may be much lower than those necessary to sterilize an area by total destruction of all organisms.

Other Types of Germicidal Radiation

U.S. Pat. No. 5,900,211 (Dunn, 1999) also notes that it is not only UVC that can be used to sterilize water and food. Dunn discusses the use of pulsed polychromatic light to inactivate organisms. Dunn uses much lower amounts of energy to inactivate an organism than would be necessary to destroy it by excessive heat. However, Dunn applies this technology only to the sterilization of food and other materials and does not contemplate it for treatment of skin or nail infections. This is presumably because of the perceived inability of the light to penetrate the skin or nails (Dunn indicates that the effectiveness of the light is dependent on its ability to penetrate a medium effectively).

Prior Art Using UVC to Kill and Inactivate Organisms

U.S. Pat. No. 6,254,625 (Rosenthal, 2001) is an apparatus to sterilize hands to prevent the spread of infectious organisms. This apparatus makes use of light to sanitize the surface of the hands to prevent infections from spreading form person to person. In all of its embodiments it consists of at least two items. It make use of light to kill organisms along with either additional light to recuperatively heal the skin that has been irradiated or the use of ozone to increase the efficiency of killing organisms. The recuperative healing light uses the phenomenon of photoreactivation whereby cells and organisms that have been damaged can repair the damage using such light of a different wavelength. The inclusion of this source of light as part of the apparatus indicates that the disease causing organisms are killed and not merely inactivated otherwise they too could repair damage by photoreactivation. Additionally, the patent does not contemplate the use of the apparatus to treat an infected area of the skin and it makes no mention of treating any infection of the nails using electromagnetic radiation. The apparatus relies on the use of ozone to kill any organisms under the nails or shielded by debris and notes incorrectly that UVC radiation will not penetrate the nail. Rosenthal appears to be unaware that germicidal UV can penetrate the skin and nails and is used to treat infections.

U.S. Pat. No. 6,283,986 (Johnson, 2001) discusses the use of UVC radiation to treat wounds. However, Johnson only applies radiation to open wounds, which can be readily exposed, and notes that "given the short wavelength of UVC, no penetration of the underlying tissue would be expected." The patent makes no mention of skin infections and mention of the nails is totally absent from the application although nail infections comprise a large part of total dermal infections. Possibly, the reason the patent only applies to wounds is that by their nature wounds are open and therefore capable of having their surfaces irradiated. It appears that Johnson is also unaware of the ability of germicidal radiation to penetrate the skin and nails.

It is the misconception that germicidal light cannot penetrate skin and nails which has in part prevented the discovery that germicidal radiation, including UVC, can indeed penetrate to a depth sufficient to be used successfully to treat skin and nail infections. While it is true that skin and nails will absorb a large percentage of UVC, enough can penetrate to successfully treat and prevent infections.

Nail Infections and Treatment

Nail infections are a particularly significant problem in the general population, affecting an estimated 5% of the overall population (approximately 15 million people). This percentage is significantly higher in the elderly age group and among athletes and other individuals who have high moisture in the area of their feet. Nail infections are often caused by fungus and this type of infection is termed onychomycosis. Currently, the preferred method for the prevention and treatment of skin and nail infections relies on application of topical medications or ingestion of medications. These medications are used to treat an existing infection, not for the prevention of an infection. Cost of treatment using medication can be between $600 and $1200 per course of treatment and can last three to six months. This is the amount of time it takes the medication to be incorporated into the nails. Another one to six months is then required for the nail to become free of infection. It should be noted that the cost noted above does not take into account doctors visits or diagnostic testing to determine if the patient can tolerate the medication (many medications can cause liver and other damage).

The problems associated with oral anti-fungal medications can be illustrated by several quotes from the clinical testing results for Itraconazole capsules (marketed under the trademark name SPORANOX® manufactured by Janssen Pharmaceutica, Inc.) which was the most prescribed anti-fungal in the U.S. in 1996. The success rate for treatment of onychomycosis of the toenail is reported as follows— "Results of these studies demonstrated mycological cure . . . in 54% of the patients. Thirty-five (35%) of patients were considered an overall success (mycologic cure plus clear or minimal nail involvement with significantly decreased signs) and 14% of patients demonstrated mycological cure (clearance of all signs, with or without residual nail deformity)." With respect to adverse reactions— "SPORANOX® has been associated with rare cases of serious hepatoxicity, including liver failure and death. Some of the cases had neither pre-existing liver disease nor a serious underlying medical condition." In a study of 602 patients treated for systemic fungal disease, "treatment was discontinued in 10.5% of the patients due to adverse events."

Although the current preferred method of treating nail infections is the use of oral medication, there are several other treatments in use. There are several topical applications that are used to treat fungal infections of the nails. However, these have an even poorer success rate than oral medications and the infections tend to re-occur.

U.S. Pat. No. 6,090,788 (Lurie, Jul. 8, 2000) is a patent to destroy fungal infections of the nails by introducing a pigment into an infected area and then to heating the pigment in the infected area with a laser in order to raise the temperature high enough to kill the organisms that have caused the infection by excessive heating. The energy listed in the preferred embodiments is from 5 to 15 J/cm$^2$ and it has a relatively long wavelength (generally 500 to 700 nm) in order to penetrate the nail. The high amount of energy is great enough to cause excessive heating of the surrounding area thus destroying the organism. However, such high energy levels also have undesirable effects on the surrounding tissue such as redness and swelling.

Lurie incorrectly notes that typical fungi do not have pigment and, therefore, cannot absorb light. However, all cells will absorb light at a wavelength of between 240 and 280 nm since the DNA in the organism will absorb light at this wavelength. Also, Lurie is not cognizant of the fact that organisms can be inactivated at much lower doses that those necessary to destroy them by excessive heat. Due to the complicated nature of the treatment, U.S. Pat. No. 6,090,788 is proposed as a method to treat an infection, not to prevent one.

Lurie notes "there is a widely recognized need for, and it would be highly advantageous to have, a phototherapy method for treating skin and nail pathogens and a pharmaceutical composition to effect same." It may be added that there is even a greater need to treat skin and nail infections using germicidal radiation only, particularly if said radiation could be effective at a much lower dose and not have the side effects associated with high energy lasers.

BACKGROUND OF INVENTION—OBJECTS AND ADVANTAGES

Accordingly, several objects and advantages of my invention are:

a) A means to treat the infected area directly thus eliminating the need to use oral medications that affect the entire body, can have serious side effects, and have only a limited success rate for treating infections.

b) A means to treat the infected area using a very small number of treatments (one to perhaps a dozen) over a short period of time (generally less than one month) as opposed to the need to ingest oral medication periodically for three months or more.

c) A means to treat an infection much more cost effectively that the current cost of $600 to $1200 per course of treatment plus the additional costs of monitoring for side effects, etc.

d) A means to treat an infection in much less time (generally less than a month) as opposed to having to wait three to six months for the medication to take effect.

e) A means, which treats the infection using a minimal amount of radiation to inactivate the organism instead of radiation treatments using a large amount of energy to destroy an infection by excessive heat. This also greatly reduces the possibility of complication arising from using excessive amounts of energy.

f) A means to directly treat infections using radiation without first having to introduce an artificial pigment into the area about to be treat. This saves time, cost, and eliminates the chance of side effects resulting from inducing the pigment.

g) A means to prevent infections before they become established. Other methods cannot be used preventatively due to their high costs, potential side effects, and the long length of time they take to act.

h) A means to prevent infections before they become established infections which is particularly valuable to those who a predisposed to infections or persons that such infections pose a significant threat.

Still further objects and advantages will become apparent from a consideration of the ensuing description and drawing.

SUMMARY OF INVENTION

The invention, a method to prevent and treat skin and nail infections, uses electromagnetic radiation to inactivate the organisms that cause infections. The method of treatment consists of irradiating the portion of skin and nail to be treated using electromagnetic radiation of a germicidal nature. The method utilizes a previously unrecognized ability of germicidal radiation to penetrate the skin and nails sufficiently to successfully treat and prevent infections. Said electromagnetic radiation damages the organisms that cause skin and nail infections and disables their ability to replicate. Without the ability to replicate the organism cannot continue to infest the skin and nails. The infection is thereby prevented if it has not yet begun and it is cured if the infection already exists. Said invention is also referred to as "method to treat infections" in this application.

DRAWINGS—FIGS. 1, 2, and 3

DRAWINGS—REFERENCE NUMBERS

10—means of providing electromagnetic radiation
12—electromagnetic radiation
14—area of skin with infection
16—area of nail with infection
18—means to prevent radiation from affecting non-infected areas of the skin and nails
20—non-infected area of skin
22—non-infected area of nail
24—opening in means to prevent radiation from affecting non-infected areas (18), said opening which permits radiation to reach the area being treated.
26—means to prevent electromagnetic radiation from damaging eyes
30—large toe of left foot of subject
32—non-infected area of toenail of left large toe (30)
34—infected area of toenail that is was black
36—infected area of toenail that was reddish-brown
38—infected area of nail bed that was black
44—former infected area almost grown out of nail

Figure 1:
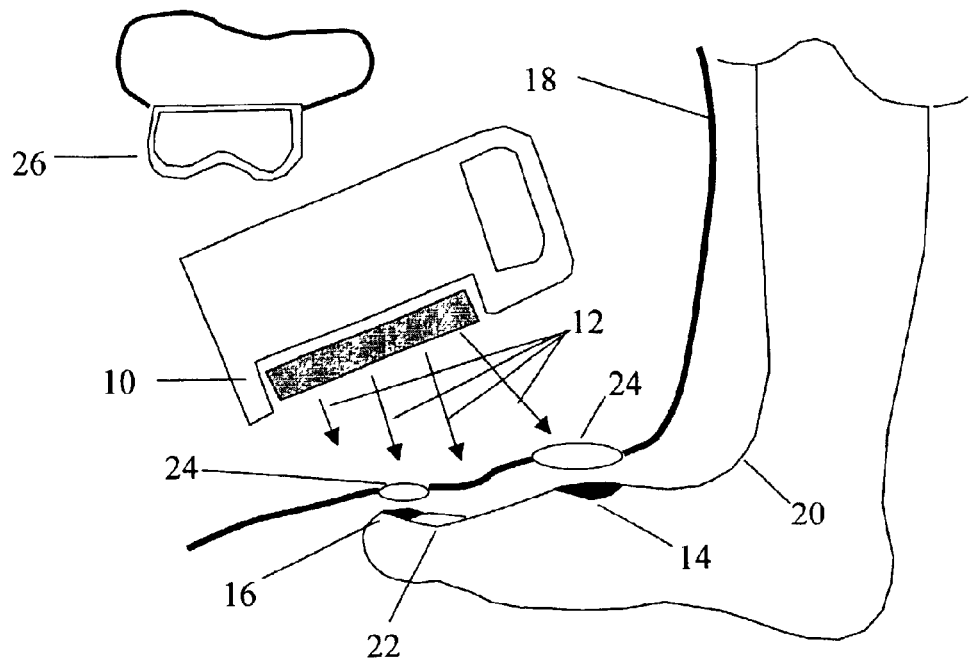
FIG. 1 is a schematic diagram of the method of treatment embodied by the invention.
Figure 2:
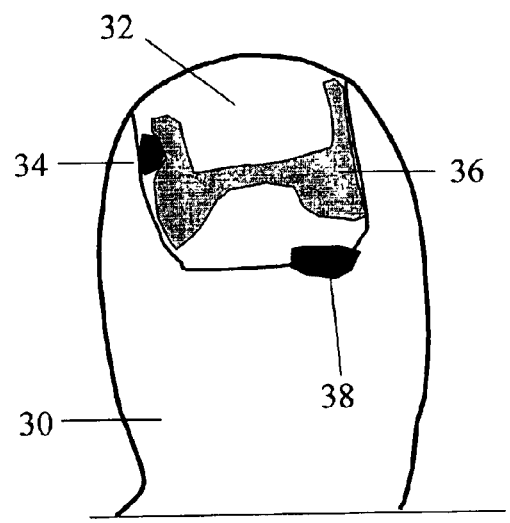
FIG. 2 is a sketch of a toenail infected with a fungal infection before treatment was applied.
Figure 3:
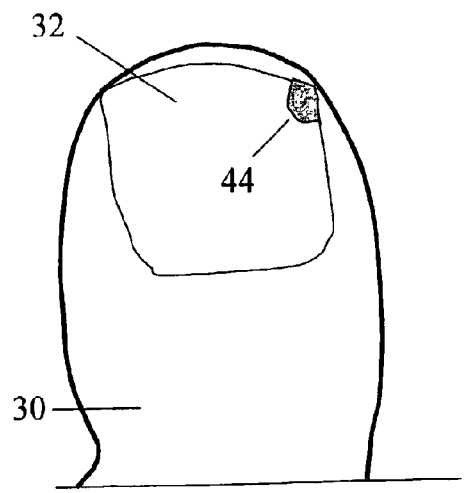
FIG. 3 is a sketch of said toenail approximately nine months after the last treatment was applied.

OPERATION—FIGS. 1, 2, and 3

The present invention to treat and prevent skin and nail infections will be described more fully hereinafter with reference to the accompanying drawing, in which a preferred embodiment of the invention is shown. This invention may, however, be embodied in many different forms and should not be construed to be limited to the embodiments set forth herein; rather these embodiments are provided so that this disclosure will be thorough and complete, and will fully convey the scope of the invention to those skilled in the art.

A preferred embodiment of the invention is illustrated in FIG. 1. The invention is a method to prevent skin and nail infections and to treat existing skin and nail infections. The method uses a previously overlooked ability of germicidal radiation to penetrate the skin and nails sufficiently to prevent and treat nail infections. The method of treatment uses a source of electromagnetic radiation 10 and the radiation 12 irradiates the area of the skin 14 and nail 16 to be treated. A means 18 can be provided to prevent the said radiation 12 from irradiating other areas of the skin 20 and nails 22 that do not require treatment. An opening 24 permits said radiation 12 to reach the infected area 14 and 16. A means 26 can also be provided to protect the eyes from the effects of the electromagnetic radiation.

Treatment can be illustrated by the application of the invention to a nail infection that occurred in the summer of 2001. FIG. 2 is a sketch of the infection of the nail 32 of the left large toe 30 when it was approximately one month old on Sep. 1, 2001 and had spread to approximately 20% of the nail. The large left toe 30 is unaffected, however, the toenail 32 has three main areas of infection 32, 34, and 36. The upper left infected area 34 was black and relatively small. The middle infected area 36 was reddish-brown and covered approximately 20 percent of the nail. The nail bed 38 was also infected and said infection extended partially below the skin.

An initial irradiation of the nail 32 was made on Sep. 5, 2001. The source of electromagnetic radiation was a low pressure mercury lamp (model G6T5) as manufactured by American Ultraviolet Company of Murray Hill, N.J. The lamp is capable of providing 11 uw/cm$^2$ at 1 meter at a wavelength of 254 nm. The lamp was used for three minutes at a distance of 4-inches from the nail 32 for an approximate dose of 37,000 uw-sec/cm$^2$. The treatment appeared to be successful in treating the large infection of the nail 36. However, infected areas of the nail, primarily the infected nail bed 38, continued to grow over the next two months necessitating additional treatments. Treatments identical to the first treatment were made on Oct. 6, 7, 8, 30, and 31 and on Nov. 1, 2001. One last treatment was made on Nov. 8, 2001 at a total dosage of approximately 100,000 uw-sec/cm$^2$ (the lamp was used for approximately 8 minutes at a distance of 4-inches from the nail). A total of 8 treatments were made applying a total dosage of approximately 360,000 uw-sec/cm$^2$ (360 mw-sec/cm$^2$ or 360 mJ/cm$^2$).

For all treatments the areas of the skin and nails 22 and 24 not being treated were covered with cloth to prevent exposure. Only very mild erythema (E0 to E1) was noted after the treatments and there was no pain during or after any of the treatments. It was noted that the nail bed 38 (where the nail connects to the skin) was significantly infected and was the area that was the most difficult to treat. By Dec. 18, 2001 it was apparent that the infections were no longer active.

FIG. 3 shows the nail 32 approximately 9 months after the last treatment. The toe 30 has not changed. The toenail 32 is now completely free of infection except for a small area of the nail in the upper right 44 which has the last part of the dead infection growing out. This area of previous infection 44 is chalky white and has no evidence of active infection.

DETAILED DESCRIPTION OF INVENTION

The method for the prevention and treatment of skin and nail infections combines the use of germicidal electromagnetic radiation with the previously unrecognized ability of said radiation to penetrate the nails and skin sufficiently to inactivate organisms.

The following descriptions of the presently contemplated best modes of practicing the invention is not to be taken in a limiting sense, but is made merely for the purpose of describing general principles of the invention. The scope of the invention should be determined with reference to the claims.

As noted above, the present invention employs germicidal radiation to prevent and treat skin and nail infections. To successfully treat these infections it is necessary to provide radiation that is germicidal in nature, is able to penetrate to the site of the infection, and is delivered for sufficient time and strength to inactivate the organism. Treatment is accomplished using the previously unrecognized ability of germicidal radiation to penetrate the skin and nails sufficiently to inactivate organisms that cause skin and nail infections. Also, although the description of the invention discusses human subjects, it is contemplated that the treatment can be used on both human and animal subjects.

Said method is capable of being used to treat and prevent all infections of the skin and nails. This includes the most common skin infections caused by *Staphylococcus aureus*, *Streptococcus pyrogenes*, *Psuedomonas aeriginosa*, and all other organisms that cause skin infections. It also includes nail infections caused by bacteria, fungi (including dermaphytes, yeasts, molds, and non-dermaphyte molds), viruses, and other microbes. Specifically, organisms causing fungal infections of the nails, said infection being termed onychomycosis, are included in the list of organisms treated by this invention. It specifically includes *Apergillus* spp., *Trichophyton rubrum*, *Trichophyton mentagrophytes*, *Trichophyton schoenleinii*, *Trichophyton tonsurans*, *Epidermophyton floccsum*, *Microsporum* spp., *Candida* spp., *Fusarium oxysporum*, *Scopulariopsis brevicaulis*, *Acremmonium* spp., and *Scytalidium dimadiaturn* which are the major causes of onychomycosis.

UVC

The most recognized form of germicidal radiation is UVC radiation in the range of 240 to 280 nm. Radiation in this range is absorbed by the RNA and DNA of a cell and damages the ability of the cell to reproduce. Other forms of radiation have also been found to inactivate organisms including sources at 180 to 1370 nm and sources that emit in a high intensity pulsed manner. Although the author does not wish to be bound by any theory of operation it is believed that germicidal light affects the ability of the cell to reproduce by damaging its genetic material or by damaging the cell so that it cannot survive and reproduce.

It has been observed that organisms vary in their resistance to the effects of germicidal radiation. For most organisms a dose of 5 to 10,000 mw-sec/cm$^2$ (5 mJ/cm$^2$ to 10 J/cm$^2$) is sufficient to completely inactivate an organism. This dose may be applied in several separate sessions, however, care must be taken that the organism does not recover and reinfest the area between treatments.

Preferentially, the radiation of choice is UVC is the range of 254 nm that can be readily produced by a low pressure mercury lamp or by a laser. This type of radiation source (generally a mercury lamp) is readily available from a number of manufacturers and there is an extensive list of inactivation doses for many organisms for this type of light. This type of radiation is the preferred form of radiation for disinfection of air in buildings such as hospitals and for disinfection of drinking water. A laser with output at 254 nm is another preferred source of radiation. A laser could be more effective that a low pressure mercury lamp since it can precisely deliver a specified dose or radiation without affecting adjacent areas. This type of laser is currently commercially available and is used for manufacturing integrated circuits among other things.

It is possible to treat a nail or skin infection using radiation without knowing what organism causes the infection. However, doing so runs the risk of not applying sufficient radiation or conversely applying too much radiation. Therefore, when treating an infection it is best to make a diagnosis of what organism is causing the infection. Once the cause of the infection is determined, the practitioner can consult the UVC charts that are available from the manufacturers of UV germicidal lamps. Many charts list have more than 50 different types of organisms listed along with the dose of UV at 254 nm that is required to inactivate them. Charts are available from the American Ultraviolet Company (Murray Hill, N.J.), from the Atlantic Ultraviolet Corporation (Hauppauge, N.Y.), other manufacturers, and research organizations. The inactivation charts provided by American Ultraviolet Company and Atlantic Ultraviolet Corporation are incorporated by reference as if fully set forth herein.

Once the infection causing organism is determined and the necessary UV dose at 254 nm is obtained from a chart, a practitioner must determine the distance from the skin the lamp must be held and the amount of time the area should be irradiated to deliver the necessary dose. Manufacturers of germicidal lamps provide formulas to determine these parameters.

Example of Treating a Skin Infection

To treat a skin infection a practitioner would generally:

Determine the cause of the infection if possible

Determine the dose of germicidal radiation necessary to treat the infection

Determine how to apply the dose or doses of radiation

Apply the dose or doses of radiation

Follow-up after treatment to determine if the infection has been stopped

Provide additional treatment as necessary

To determine the cause of infection, a practitioner would either culture the organism from a sample or would make a clinical determination based on visual observations.

Next a practitioner must determine the dose of germicidal radiation necessary. Inactivation doses are available in charts for many of the organisms that cause skin infections such as *Staphylococcus aureus* (6,600 uw-sec/cm$^2$ to inactivate), *Streptococcus pyogenes* (4,200 uw-sec/cm$^2$ to inactivate), and *Psuedomonas aeriginosa* (10,500 uw-sec/cm$^2$ to inactivate). Additionally, new organisms are being added all the time as more research is directed to the germicidal effects of UVC light. If an organism is not listed on the chart it may be possible to infer a probable inactivation dose. For example, of the more than 50 types of bacteria listed on one manufacturer's chart, all the inactivation doses ranged from 2,500 to 26,400 uw/cm$^2$ (with the exception of Anthrax spores which are especially difficult to treat and have a published range of 9,400 to 135,000 uw/cm$^2$ to inactivate). Therefore, if a person had a bacterial infection and it was not possible to determine its cause, a practitioner could irradiate the infection at the high end of the range to inactivate the infection. As germicidal treatment of infections becomes more common it is expected that the inactivation doses of all major organisms will be determined with great accuracy.

Skin infections are often difficult to treat due to encrustations and debris and due to the sensitivity of the area. While germicidal radiation is attenuated by encrustations and debris the radiation, if applied in the proper dose, enough should be able to penetrate sufficiently to have a beneficial effect. However, good practice would dictate that as much as possible all encrustations and debris be removed to maximize the benefits of the radiation. It may also be necessary to spread out treatments in particularly deep infections so that the surface of the infection may heal and permit easier application of radiation to the deeper levels (clear skin will permit radiation to pass more easily than thick and opaque encrustations.

If a practitioner determined that the infection was caused by *Staphylococcus aureus* (a common cause of skin infections) she could then consult a chart and determine the inactivation dose was 6,600 uw-sec/cm$^2$. This can be achieved using a G6T5 low pressure lamp available from American Ultraviolet Company (AUC). The lamp uses fixtures and ballasts that are similar to fluorescent lights. The lamp provides 11 uw/cm$^2$ at a distance of one meter. If the lamp is held 6-inches from the infection the multiplication factor to convert the applied radiation 1-meter to the amount applied at 6-inches is obtained from a chart supplied by American Ultraviolet Company. This factor is 12. Therefore a G6T5 lamp held 6-inches from an infection will irradiate 132 uw/cm$^2$ (11 uw/cm$^2$ times the conversion factor of 12). Thus, a practitioner would need to irradiate a person for 50 seconds (6,600 uw-sec/cm$^2$ divided by 132 uw/cm$^2$) at a distance of 6-inches from the infection to inactivate an organism. In reality, however, it may be desirable to irradiate a person using approximately twice the nominal value of radiation necessary to inactivate the organism as a factor of safety. It may also be desirable to apply the total radiation in two sessions, each of 6,600 uw-sec/cm$^2$ to minimize the daily doses of radiation while also applying a factor of safety of two.

Once the radiation is applied, the practitioner would schedule regular follow-up appointments to monitor the status of the infection. If the infection continued to spread, the practitioner would apply additional doses of radiation to inactivate the organism causing infection.

Example of Treating a Nail Infection

Treating a nail infection is similar to treating a skin infection with one additional item. When treating a nail infection, account must be taken of the transparency of the nail and its ability to transmit radiation. While a non-infected clear nail may transmit a relatively large amount of radiation due to its semi-transparent nature, a nail that has been darkened or thickened by infection will be able to transmit significantly less. Therefore, if possible it is desirable that a small sample of the nail be obtained and tested to determine the amount of light it can transmit. The test should use the wavelength of the light that will be used for treatment since light of different wavelengths has varying ability to penetrate the nail. In the absence of being able to test the actual nail, a practitioner with experience can estimate the amount of light that can be transmitted through the infected nail. In severely infected and thickened nails it is possible that less than ten percent of the light might pass and that the dosage of electromagnetic radiation would have to be adjusted accordingly. For example, if it was determined that the nail could only transmit ten percent of light at 254 nm and the organism required a dose of 99,000 uw-sec/cm$^2$ (*Aspergillus flavus* is a fungus that causes some nail infections and it requires this dose of UV254 to inactivate it) then at total of 10 times that amount of energy, or 990,000 uw-sec/cm$^2$ (990 mw-sec/cm$^2$) would need to be applied to inactivate the organism. A factor of safety would also need to be applied similar to that for skin infections.

Prevention of Skin and Nail Infections

Additionally, microbial infections can be prevented by the periodic application of electromagnetic radiation to prevent incipient infections from occurring. This would be particularly desirable in populations prone to fungal infections (such as diabetics and the elderly) and those who require constant monitoring (such as those in hospitals and nursing homes). It would also be very desirable for those whose health could be significantly threatened by a fungal infection (such as diabetics or immunocompromised individuals). Fungal infections of the nails in a diabetic person can progress and associated complications can lead to amputation of a finger or toe. The dose necessary to prevent fungal infections would be significantly less than that necessary to eradicate a full blown infection. The dose would be approximately in the range of half of the standard dose and should be sufficient to inactivate approximately 99% of the organisms that may be present. This dose would be applied on a periodic basis (daily, weekly, monthly, or quarterly depending on the estimated risk of infection and the dose applied) to help keep a person infection free.

The foregoing is illustrative of the present invention and is not to be construed to be limiting thereof. Although a few exemplary embodiments of this invention have been described, those skilled in the art will readily appreciate that many modifications are possible in the exemplary embodiments without materially departing from the novel teachings and advantages of this invention.

Other Forms of Germicidal Radiation to Treat Infections

The description of the invention discusses UVC light to prevent and treat infections. However, any electromagnetic radiation that has antimicrobial effects is also contemplated by this method to treat infections. An example of electromagnetic radiation other than UVC that can be used to inactivate organisms is broad spectrum, high intensity, pulsed light. Page 5 of *Kinetics of Microbial Inactivation for Alternative Food Processing Technologies* (U.S. Food and Drug Administration Center for Food Safety and Applied Nutrition, Jun. 2, 2000) notes that a single pulse of such light (with a wavelength of 170 to 2600 mn) with an intensity as small as 1.25 J/cm$^2$ is sufficient to inactivate *Staphylococcus aureus*. This is significantly less that the 6.6 J/cm$^2$ of UV at 254 nm required and makes the use of this type of radiation particularly attractive. This type of light may also penetrate more easily (longer wavelength light penetrates more easily than short wavelength light) and is better tolerated than UVC which is also advantageous.

PurePulse Technologies, Inc. sells a pulse light that can deliver this type of radiation under the trademark PUREBRIGHT™. This type of light generally has a DC power supply which charges capacitors, a switch which controls the discharge of the capacitors, a trigger circuit which permits the capacitors to be discharge at preprogrammed time intervals, a manual discharge mode, and one to four flash lamps mounted in reflectors to direct the light emitted from the lamps. This configuration could be modified and refined to be more suitable for use treating skin and nail infections. The method to use this device would be similar to that described above for using a low-pressure mercury lamp that is describe above. Research is currently being conducted on a wide range of organisms to determine the energy necessary to inactivate each organism and what is the best way to apply such energy (i.e. one large pulse or a number of smaller pulses).

The effectiveness of multi-spectrum germicidal light for inactivation of organisms at lower overall doses than UVC alone indicates that other parts of the spectrum have germicidal properties. The exact inactivation mechanism is not known, however, it probably is a combination of several mechanisms that act together to render the cell inactivated or incapable of reproducing. Although the author does not wish to be bound as to the mechanism of inactivation used, several observations may be made. In addition to probable damage to the organism's genetic material, the multi-spectrum light could damage other components of the organism necessary to its vital functions. It may also provide instantaneous heating of small areas in the cell which would not kill the organism by high heat but which are nonetheless effective in damaging the cell wall and inactivating the organism.

It is likely that there are certain types of radiation that are more effective than others at inactivating organisms or preventing them from reproducing. These types of radiation are likely contained in the range of pulsed light (170 to 2600 nm) but other parts of the spectrum may also be germicidal. Therefore, the proposed method to prevent and treat skin and nail infections claims any forms of electromagnetic radiation that can be used germicidally to inactivate an organism or prevent it from reproducing.

DESCRIPTION OF PREFERRED EMBODIMENTS

First Preferred Embodiment

In a preferred embodiment, the radiation is that which is necessary to inactivate the organisms that cause infections of the skin and nails. In a preferred embodiment of the invention the organisms inactivated are those that cause infections of the skin and nails. These organisms include bacteria, fungi (including dermaphytes, yeasts, molds, and non-dermaphyte molds), viruses, and other microbes. Specifically, organisms causing fungal infections of the nails, said infection being termed onychomycosis, are included in the list of organisms treated by this invention.

In a preferred embodiment, it may be necessary to irradiate the skin and nails for several times in order to completely inactivate the organisms. The electromagnetic radiation in the preferred embodiment consists of radiation in the UVC range (100 to 280 nm and more specifically in the range of 240 to 280 nm) that is capable of rapidly inactivating an organism. In a preferred embodiment, the UVC source may be a low, medium, or high pressure mercury vapor lamp or a laser.

In a preferred embodiment, the amount of irradiation received during one treatment will in the approximate range of 5 to 10,000 mw-sec/cm$^2$. In a preferred embodiment it may be desirable to apply the radiation in several sessions.

Second Preferred Embodiment

Another preferred embodiment of the method to treat infections of the skin and nails involves irradiating the infected area using from 37 to 100 mJ/cm$^2$ per treatment using a lamp emitting 254 nm over a period of time for a total applied radiation does of 350 to 400 mJ/cm$^2$.

The electromagnetic radiation is a specific composition of matter that is used to prevent and treat skin and nail infections. In a preferred embodiment the radiation can be applied to humans and animals. The electromagnetic radiation in a preferred embodiment consists of radiation in the UVC range (100 to 280 nm and more specifically in the range of 240 to 280 nm) that is capable of rapidly inactivating an organism. In a preferred embodiment, the UVC source may be a low, medium, or high pressure mercury vapor lamp or a laser.

Third Preferred Embodiment

In an additional preferred embodiment the electromagnetic radiation used may be from a polychromatic pulsed source such as those used to disinfect food and instruments. In additional preferred embodiments any electromagnetic radiation can be used which is capable of inactivating the infection causing organisms, is able to penetrate sufficiently, and is safe for exposure to humans and animals in the doses contemplated.

Other Preferred Embodiments

For particularly difficult infections, it could be beneficial to combine the said method of treatment with adjunct therapy including the application of oral and topical medications. This combination may work synergistically to effect a cure in a shorter period of time, in a more complete manner, or in a manner that creates less probability of relapse. Accordingly, a preferred embodiment is to combine the said method of treatment with adjunct therapy including the application of oral and topical medications as deemed appropriate by those skilled in the field.

Other preferred embodiments include delivering all the necessary radiation in one dose of approximately 50 to 1000 mJ/sec$^2$ using a wavelength of between 240 and 280 nm.

Substantially more radiation than this may be necessary in particularly difficult infections.

Other preferred embodiments may include dosages of from 5 mJ/cm$^2$ to 50 J/cm$^2$ if the radiation is of a wavelength that it can be applied safely in higher doses (this would be most applicable if multi-spectrum light is used). The light may be of multiple wavelengths and may be coherent or incoherent, and may be pulsed.

Alternative Embodiments

The electromagnetic radiation in an alternative embodiment may be from UVA radiation (315 to 400 nm ).

The electromagnetic radiation in an alternative embodiment may be from UVB (280 to 315 nm) radiation.

The electromagnetic radiation in an alternative embodiment may also be from the visible part of the spectrum.

The electromagnetic radiation in an alternative embodiment may be from infrared radiation.

The electromagnetic radiation in an alternative embodiment may be from radiation from a combination of visible and non-visible parts of the light spectrum.

The electromagnetic radiation in an alternative embodiment may be from a pulsed source including a xenon pulse source or a laser.

The electromagnetic radiation in an alternative embodiment may be incoherent or coherent such as a laser.

The electromagnetic radiation in an alternative embodiment may be single spectrum or multi-spectrum.

In an alternate embodiment, the amount of irradiation received during one treatment may be substantially more or less than the 5 to 10,000 mw-sec/cm$^2$ of the preferred embodiment. In all circumstances the total amount of irradiation shall be within the limits deemed safe by the medical community for treatment of a disease or infection.

SUMMARY, RAMIFICATIONS, AND SCOPE

Accordingly, the reader will see that this invention can be used to prevent and treat a wide variety of skin and nail infections. It has the following advantages over the current method of treatments for these infections:

With respect to treatment using oral medications, the invention eliminates unwanted and potentially dangerous side effects (such as liver problems) that such medications can cause.

With respect to treatment using oral medications, the invention uses a very small number of treatments (one to perhaps a dozen) to eliminate the infection while medications must be taken continuously for several months.

With respect to treatment using oral medications, the proposed treatment has the potential to be significantly less expensive than the current cost of $600 to $1200 for medicine.

With respect to treatment using oral medications, the infection can be eliminated in much less time since the course of treatment would vary from approximately one day to one month whereas the medications must be taken from three to six months.

With respect to treatment by inducing a pigment and using a high energy light to destroy an infection by excessive heat, the invention eliminates the need to separately induce a pigment in the organism before treatment begins. This saves time, cost, and eliminates the chance of side effects resulting from inducing the pigment.

With respect to treatment by inducing a pigment and using a high energy light to destroy an infection by excessive heat, the invention eliminates the need for a large amount of energy to destroy the organisms by excessive heat which may also cause damage and discomfort to the patient. The invention uses significantly less energy and thus has a much lower risk of complications.

With respect to other treatments used for existing infections, this treatment can also be used periodically to prevent infections from becoming established. This is particularly desirable for those who are predisposed to skin and nail infections or persons that such infections pose a significant threat.

Although the descriptions above contain many specificities, these should not be construed as limiting the scope of the invention but merely as providing illustrations of some of the presently preferred embodiments of this invention. For example, other sources of radiation may be used if they have the properties necessary to inactivate organisms, penetrate sufficiently, and are safe to humans or animals, etc.

Thus the scope of this invention should be determined by the appended claims and their legal equivalents, rather than by the examples given.

I claim:

1. A method for the treatment of nail infections of a user caused by microbes comprising the step of applying electromagnetic radiation in the range of 100 to 280 nm to an infected nail of a user for a time and at a proximity and intensity sufficient to render the microbes substantially incapable of reproducing by at least one of disruption of cellular processes of the microbes or damaging the genetic material of the microbes while insufficient to kill the microbes.

2. The method of claim 1 wherein said nail infections are caused by microbes selected from the group consisting of bacteria, fungi, yeast, molds and viruses.

3. The method of claim 1 wherein said electromagnetic radiation is generated by a mercury lamp or a laser.

4. The method of claim 1 further comprising the step of providing means for preventing said electromagnetic radiation from affecting the user's eyes and any area of the user's skin and nails not being treated.

5. The method of claim 1 wherein said treatment is supplemented with subsequent oral and topical medications to enhance the effectiveness of said treatment.

6. The method of claim 1, wherein said electromagnetic radiation is generated by an artificial light source providing substantially all of the microbe-affecting radiation in the form of UVC light.

7. The method of claim 1, wherein said electromagnetic radiation is provided for a predetermined time and intensity which is sufficient to inactivate substantially all of the nail-infection-causing microbes.

8. A method for the prevention or treatment of microbial nail infections of a user caused by microbes comprising the step of applying electromagnetic radiation to a nail infected by at least unpigmented microbes that may become infected for a predetermined time and at a proximity and intensity sufficient to render the microbes substantially incapable of reproducing without destroying the microbes, wherein substantially all of the radiation affecting the microbes during the step of applying electromagnetic radiation is provided in the range of 100 nm to 315 nm directly to the microbes to excite and heat the unpigmented microbes without requiring the addition of an external agent such as a pigment, light absorbing material, topical agent or subtopical agent to heat the microbes.

9. The method of claim 8 wherein said microbial infections to be prevented are those caused by microbes selected from the group consisting of bacteria, fungi, yeast, molds and viruses.

10. The method of claim 8 wherein said electromagnetic radiation is UVC light in the range of 100 to 280 nm.

11. The method of claim 8 wherein said electromagnetic radiation is generated by a mercury lamp.

12. The method of claim 8 wherein said electromagnetic radiation is generated by a low pressure mercury lamp emitting at substantially 254 nm.

13. A method for the treatment of a user's and nail infections caused by microbes comprising the step of applying a dose of electromagnetic radiation in the range of 100 nm to 315 nm to an infected area of the user's skin, whereby radiation in the range of 100 nm to 315 nm directly heats the DNA or RNA of the microbes, and wherein the dose of electromagnetic radiation renders the microbes substantially incapable of reproducing by altering one of the DNA and RNA without killing the microbes.

14. The method of claim 13 wherein said infections are caused by microbes selected from the group consisting of bacteria, fungi, yeast, molds, viruses, and microbes which specifically contribute to acne.

15. The method of claim 13 wherein said electromagnetic radiation is in the range range of 240 nm to 280 nm.

16. The method of claim 13 further including the step of calculating theoretical loss corrections to compensate for electromagnetic radiation energy losses caused during transmission through the infected nail, prior to applying the amount of the dose of electromagnetic radiation to the infected nail.

17. The method of claim 12 further comprising the step of providing means for preventing said electromagnetic radiation from affecting the user's eyes and any area of the user's skin and nails not being treated.

18. The method of claim 13 wherein said treatment is supplemented with oral and topical medications to enhance the overall effect of said treatment subsequent or prior to the electromagnetic radiation of the user's skin.

19. A method for the treatment of nail infections of a user caused by microbes comprising the step of applying a dose of electromagnetic radiation in the range of 100 nm to 280 nm to an infected nail of a user sufficient to render the microbes substantially inactivated by damaging the genetic material of the microbes or by disruption of cellular processes of the microbes without destroying the microbes.

20. The method of claim 19, the dose of electromagnetic radiation is less than half of the radiation required to kill the microbes.

21. A method for the treatment of nail infections of a user caused by microbes comprising the step of applying a dose of electromagnetic radiation in a wavelength less than 400 nm capable of directly heating the DNA or RNA of microbes infecting a nail of a user wherein the dose of electromagnetic radiation renders the microbes substantially incapable of reproducing wherein said dose of electromagnetic radiation is less than half of the radiation sufficient to kill the microbes.

22. The method of claim 21, wherein the reproductive ability of the microbes is damaged by disrupting the cellular processes of the microbes.

23. The method of claim 20, wherein the reproductive ability of the microbes is damaged by sterilizing the microbes.

* * * * *